United States Patent
Grodzki

(10) Patent No.: US 10,345,411 B2
(45) Date of Patent: Jul. 9, 2019

(54) FREQUENCY MONITORING OF GRADIENT PULSES DURING MAGNETIC RESONANCE IMAGING

(71) Applicant: Siemens Aktiengesellschaft, Munich (DE)

(72) Inventor: David Grodzki, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 1140 days.

(21) Appl. No.: 14/669,332

(22) Filed: Mar. 26, 2015

(65) Prior Publication Data
US 2015/0276904 A1    Oct. 1, 2015

(30) Foreign Application Priority Data

Mar. 28, 2014    (DE) ................ 10 2014 205 888

(51) Int. Cl.
*G01R 33/54*     (2006.01)
*G01R 33/385*    (2006.01)
*A61B 5/055*     (2006.01)

(52) U.S. Cl.
CPC .......... *G01R 33/543* (2013.01); *A61B 5/055* (2013.01); *G01R 33/385* (2013.01); *G01R 33/3854* (2013.01)

(58) Field of Classification Search
CPC .......... G01R 33/5611; G01R 33/543; G01R 33/56563; G01R 33/50; G01R 33/5602
USPC ........................................ 324/309
See application file for complete search history.

(56) References Cited

U.S. PATENT DOCUMENTS

| | | | | |
|---|---|---|---|---|
| 4,471,305 A * | 9/1984 | Crooks | ................ | G01N 24/08 324/309 |
| RE33,259 E * | 7/1990 | Crooks | ................ | G01R 33/50 324/307 |
| 5,291,610 A * | 3/1994 | Hoenninger, III | ..... | G01R 33/54 712/226 |
| 6,400,157 B1 * | 6/2002 | Bonanni | ............... | G01R 33/54 324/309 |
| 6,803,762 B2 * | 10/2004 | Shah | ..................... | G01R 33/50 324/307 |
| 7,825,661 B2 * | 11/2010 | Blanz | ................... | G01N 24/081 324/307 |
| 8,723,518 B2 * | 5/2014 | Seiberlich | ............ | G01R 33/543 324/307 |
| 8,849,372 B2 * | 9/2014 | Wald | .................. | G01R 33/5601 324/307 |
| 8,922,209 B2 * | 12/2014 | Alford | ................. | G01R 33/445 324/309 |
| 9,041,393 B2 * | 5/2015 | Warntjes | ........... | G01R 33/5602 324/307 |
| 9,235,202 B2 * | 1/2016 | Heid | .................... | G01R 33/543 |

(Continued)

*Primary Examiner* — Christopher P McAndrew
(74) *Attorney, Agent, or Firm* — Schiff Hardin LLP

(57) ABSTRACT

Machine control parameters of a magnetic resonance apparatus are selected that influence the timing sequence of gradient pulses of the system's gradient system when a magnetic resonance measurement sequence is executed. The machine control parameters are compared with reference control parameters that indicate an increased mechanical force flow in the gradient system when the MR measurement sequence is being executed. As a function of the comparison, the MR measurement sequence is executed selectively with the selected machine control parameters.

9 Claims, 4 Drawing Sheets

(56) References Cited

U.S. PATENT DOCUMENTS

| | | | |
|---|---|---|---|
| 9,285,445 B2* | 3/2016 | Wong | G01R 33/4836 |
| 9,645,216 B2* | 5/2017 | Heismann | G01R 33/3854 |
| 9,797,970 B2* | 10/2017 | Zhou | G01R 33/4836 |
| 2006/0244452 A1* | 11/2006 | Den Boef | G01R 33/3621 |
| | | | 324/322 |
| 2008/0157765 A1* | 7/2008 | Fontius | G01R 33/3415 |
| | | | 324/309 |
| 2008/0265884 A1* | 10/2008 | Miyazaki | G01R 33/543 |
| | | | 324/309 |
| 2009/0256570 A1* | 10/2009 | Zelinski | G01R 33/4836 |
| | | | 324/314 |
| 2012/0194185 A1 | 8/2012 | Ritter | |
| 2013/0177972 A1* | 7/2013 | Green | C12M 21/08 |
| | | | 435/288.7 |
| 2013/0271139 A1 | 10/2013 | Grodzki et al. | |
| 2014/0111200 A1* | 4/2014 | Grodzki | G01R 33/543 |
| | | | 324/309 |
| 2014/0232396 A1 | 8/2014 | Grodzki et al. | |

\* cited by examiner

FREQUENCY MONITORING OF GRADIENT PULSES DURING MAGNETIC RESONANCE IMAGING

BACKGROUND OF THE INVENTION

Field of the Invention

The invention concerns techniques for selectively carrying out a magnetic resonance measurement sequence with specific machine control parameters of a magnetic resonance system, as a function of a comparison of the machine control parameters with reference control parameters that are stored in a database.

Description of the Prior Art

An MR measurement sequence is typically carried out as part of magnetic resonance (MR) imaging. The MR measurement sequence includes—as well as radio frequency pulses and read-out windows, for example—the switching (activation) of gradient pulses of a gradient system, i.e. the time-dependent application of gradient fields by feeding power to gradient coils of a gradient system. The switching of the gradient pulses typically enables local encoding of the MR data acquired as part of MR imaging to be achieved. With typically dimensioned gradient systems it can be necessary for currents of up to 900 Amperes to flow through the gradient coils.

Such currents, or comparably high currents that flow through the gradient coils—especially in conjunction with gradient pulses switched rapidly over time—can give rise to significant technical problems. It can thus be necessary during an MR measurement sequence to switch the gradient pulses within a few milliseconds. The rapid switching of the gradient pulse results in a correspondingly rapid change in the gradient fields employed. The strong and rapid change of these magnetic fields over time typically result in significant mechanical force influences in the gradient system. This frequently results in vibrations and mechanical distortions of the gradient coils, thus generally in mechanical force paths, which can be transmitted to surrounding components of the magnetic resonance system. As a result of such mechanical force paths, a large amount of noise can develop in and around the magnetic resonance system. The result is noise stress for the patient, so that countermeasures can be necessary, otherwise the comfort of the patient is reduced. An (acoustic) frequency spectrum of such mechanical movements corresponds in such cases to a Fourier transformation of a timing sequence of the gradient pulse during execution of the magnetic resonance measurement sequence. As a result of resonance effects of the gradient system or the magnetic resonance scanner, it can occur that the switching of a timing sequence of gradient pulses with specific frequency portions in so-called forbidden frequency bands has especially great effects, i.e. causes an increased flow of mechanical force in the gradient system. Thus, in such a case, the result can be an especially large amount of noise developing, strong vibrations, or an increased amount of heat developing. If the basic magnetic field is generated by superconducting coils in a cryostat, the result of a large amount of heat developing can be evaporation of coolant, e.g. helium, for the cryostat. Therefore efforts are being made, when carrying out the MR measurement sequence, to avoid a timing sequence of the gradient pulses that results in such an increased mechanical force flow in the gradient system.

There are various known solutions to this problem. For example, before carrying out the MR measurement sequence, it is possible to analyze and evaluate the timing sequence of the gradient pulses and in this way determine, or predict computationally, which frequencies are likely to be excited. In order to avoid resonance effects or increased mechanical force flow in the gradient system, the measurement sequence developer is typically obliged to avoid specific forbidden frequency bands. This can be implemented, for example, by specific time spacings between spin echoes or gradient echoes not being allowed. Such known techniques have the disadvantage that the frequency spectrum that is excited by the timing sequence of the gradient pulses is able to be computed only to a limited extent, or with comparatively high computing outlay. This can restrict the practicality of such techniques, especially with limited resources as regards computing capacity and/or time.

Therefore, in a further known approach, the excited frequencies are monitored with a so-called frequency monitor while the MR measurement sequence is being carried out. Such frequency monitoring checks the excited frequencies for the different gradient axes. Frequency monitoring can be implemented for example by a real-time Fourier transformation of the timing sequence of the gradient pulses, especially for example the timing sequence of the current flows through the gradient coil. As part of the real-time frequency monitoring for example at least one forbidden frequency band $\Delta\omega$ and an associated maximum allowed current strength $A_{max}$ can be predetermined. If $A_{max}$ is exceeded when the MR measurement sequence is carried out in the corresponding forbidden frequency band $\Delta\omega$ the carrying out of the MR measurement sequence is interrupted. Such aborting of the carrying out of the MR measurement sequence can be disadvantageous for the performance of the MR system. Thus, MR data acquired before the sequence abortion can become unusable and it can be necessary subsequently to create a new MR measurement sequence. All this can be time-intensive and susceptible to errors. If, for example, the MR measurement sequence is not changed sufficiently, or the same MR measurement sequence is carried out again at a later point in time (for example by another user), then the same error can occur once again.

SUMMARY OF THE INVENTION

Therefore, there is a need for improved techniques of frequency monitoring of gradient pulses in MR imaging. In particular there is a need for such techniques that bring about a reliable and robust avoidance of exciting frequencies by a timing sequence of gradient pulses in a forbidden frequency band, in order in this way to avoid an increased mechanical force flow in the gradient system. There is a need for less computing-intensive yet still accurately-functioning techniques.

In accordance with one aspect, the invention concerns a method for MR imaging by carrying out an MR measurement sequence by operation of an MR scanner. The method includes the selection of machine control parameters of the MR scanner. The machine control parameters influence the timing sequence of gradient pulses of the gradient system of the MR scanner during execution of the MR measurement sequence. The method further includes comparison of the machine control parameters with reference control parameters that are stored in, and accessed from, a database. The reference control parameters indicate an increased mechanical force flow in the gradient system when a corresponding MR measurement sequence is being carried out. The method further includes the selective implementation of the MR measurement sequence with the selected machine control parameters as a function of the comparison.

In other words, the machine control parameters can determine the timing sequence of events of the MR measurement sequence and the events themselves or boundary conditions when the MR measurement sequence is being executed. For example the machine control parameters can be able to be set as part of a measurement protocol for preparing the MR measurement sequence. The machine control parameters can influence, for example, spacings in time between different gradient pulses. The machine control parameters can additionally, for example, determine other events of the MR measurement sequence, thus for example radio-frequency pulses or read-out windows. The machine control parameters, in addition to influencing time spacings between different gradient pulses, can influence amplitudes of the different gradient pulses. In other words, the timing sequence of the gradient pulses can be defined both via time spacings between the individual gradient pulses and via specific characteristics of the individual gradient pulses, such as shape, duration and amplitude. The timing sequence of the gradient pulses can be distinguished for different gradient axes, such as along phase encoding, slice selection and readout direction. It would be possible, for example, to provide different machine control parameters for the different gradient axes; it would however also be possible for the machine control parameters for example, by implicit or explicit linkage, to describe the timing sequence along the different gradient axes in summary. The machine control parameters can further describe boundary conditions of carrying out the MR measurement sequence, such as e.g. measuring time, type of gradient system and/or MR system etc.

The relevant remarks that have been made above in relation to the machine control parameters can also apply to the reference control parameters. In particular the reference control parameters can describe the same physical/technical characteristics as the machine control parameters. A number of sets of reference control parameters can be stored in the database. The comparison can be carried out with all or parts of the number of sets of reference control parameters stored in the database. If the database includes a number of sets of reference control parameters, the machine control parameters can be compared in each case with an associated set of reference control parameters.

The reference control parameters can indicate explicitly or implicitly that the execution of a corresponding MR measurement sequence, i.e. on the basis of the reference control parameters, will result in frequencies in a forbidden frequency band being excited, or will result in resonance effects being caused. The increased mechanical force flow can be defined, for example, in relation to an average value over a relevant frequency range. The increased mechanical force flow could also be an increase in relation to a predetermined threshold value. In other words and in general terms, the increased mechanical force flow can characterize a mechanical resonance in the gradient system and, if necessary, in surrounding components of the MR apparatus.

In general, a variety of techniques can be employed for comparing the machine control parameters with the reference control parameters. In a simple exemplary embodiment, the machine control parameters can be checked for identity with the reference control parameters. Thus, if it is established that there are reference control parameters stored in the database which are identical to the machine control parameters, then execution of the MR measurement sequence can be dispensed with for example. This is the case since it can be expected that execution of the MR measurement sequence on the basis of the machine control parameters would result in the increased mechanical flow of force, as indicated by the identical reference control parameters. This could result, for example as part of a real-time frequency monitoring, in the execution of the MR measurement sequence being aborted, and thus would result in data losses of the MR data.

As well as such an identity check, other techniques can be taken into consideration as part of the comparison of the machine control parameters with the reference control parameters. Thus, it is possible, for example, for specific tolerance ranges or predetermined deviations between individual or all of the machine and corresponding reference control parameters to be taken into consideration; thus, even without full identity between the machine control parameters and the reference control parameters, the execution of the MR measurement sequence could be dispensed with. This can be based on the knowledge that even slight deviations with respect to a few or all machine control parameters do not always prevent the occurrence of excitation in a forbidden frequency band.

As part of such consideration of deviations between the machine control parameters and the reference control parameters, it is further possible to undertake a weighting of the deviation with respect to specific machine control parameters. In other words, for various machine control parameters, a different value of the weighting in relation to the selective execution can be employed as being significant to the decision. This can be based on the knowledge that there can be specific machine control parameters that have an increased influence on the excitation frequencies in a forbidden frequency band; especially by comparison with other machine control parameters, which can be less important with respect to increased force flow in the gradient system.

Different effects can be achieved by the techniques described herein. Thus, it is possible, for example, to establish reliably, even before the MR measurement sequence is executed, whether an increased mechanical force flow in the gradient system is to be expected with the corresponding machine control parameters. The user of the MR system then can already react accordingly at the planning stage of the MR measurement sequence and carrying out the MR measurement sequence with corresponding potential loss of MR data can be prevented. A prospective frequency monitoring can thus be implemented. At the same time the frequency monitoring can be comparatively less computation-intensive, particularly in comparison to techniques in which an MR measurement sequence is checked computationally from resonance effects. The comparison with the reference data, i.e. with an empirical data basis, can be designed less computationally intensive. At the same time a learning procedure can be achieved. It is thus possible, by suitable maintenance of reference control parameters in the database that caused an MR measurement sequence to be aborted as a result of increased mechanical force flow, to constantly expand the data basis by storing further empirically-established-as-unsuitable reference control parameters. Thus a more precise frequency monitoring can be implemented.

In general it is possible for the database to be stored locally or to be stored on a central server. For example in the latter case it is possible for a number of MR apparatuses to be able to access the stored reference control parameters or be able to store new reference control parameters. This can allow the frequency monitoring to be designed even more precisely.

As described above, the type and number of the machine control or reference control parameters considered is not particularly restricted. Thus, in general, a larger (or smaller) number of considered machine control and reference control parameters can result in a higher (or lower) accuracy in the frequency monitoring being achieved. For example the machine control parameters and the corresponding reference control parameters can be selected from the following group: Echo time TE, repetition time TR, slice number of measured slices, slice thicknesses of measured slices, bandwidth during readout of MR data, type of MR measurement sequence, pulse duration of radio frequency pulses, resolution, amplitude of the gradient pulses, current strength through the gradient coils of the gradient pulses, switching rate of gradient pulses, and type of MR apparatus.

It would be further possible for such machine control parameters and/or reference control parameters to be stored associated with the forbidden frequency ranges in which the increased mechanical force flow in the gradient system is indicated. Such information can also be implicitly associated, for example, with the type of the MR apparatus and/or a type of the gradient system. In this way it can prospectively be checked whether an actually relevant forbidden frequency range might possibly be excited.

The echo time TE can define, for example, a time between an excitation radio-frequency (RF) pulse and a read-out window. The repetition time TR can for example define a period of time between two sequentially irradiated RF pulses. The slice number of measured slices can for example define an absolute number of the irradiated RF pulses or switched gradient pulses. The slice thickness of measured slices can result, for example, in a level time or duration of a flat top of gradient pulses. The same also applies for the bandwidth during reading out of the MR data. The type of MR measurement sequence can for example distinguish explicitly or implicitly between spin echo or gradient echo MR measurement sequences. Other MR measurement sequences, as are basically known to those skilled in the art, are also possible. The pulse duration of the RF pulses can for example describe a period of time within which an amplitude envelope of the RF pulse is significantly different from 0. The resolution can designate, for example, a local resolution and be proportional to an inverse sampling rate. The amplitude of the gradient pulses can for example be proportional to a current strength which flows through the gradient coils during the use of the gradient pulses. The switching duration of the gradient pulses, known as the slew rate, can for example designate a period of time of edges of the gradient pulses.

As is evident from the above description, the type and number of machine control or reference control parameters is not especially restricted. Also, in view of this factor, it can be possible—via the identity comparison discussed above, if necessary taking account of tolerances—to implement more comprehensive techniques as part of the comparison of the machine control parameters with the reference control parameters. For example, such techniques can result in a more precise prediction of whether an increased mechanical force flow is to be expected in the gradient system.

Thus, for example, the comparison can include determining a measure of distance between the machine control parameters and the reference control parameters and making a threshold value comparison of the specific measure of distance with a predefined threshold value. The selective execution of the MR measurement sequence can take place as a function of a result of the threshold value comparison. In other words, the measure of distance can designate a metric that is defined in the area of the machine control and reference control parameters. Depending on whether the threshold value comparison has a positive or negative result, the MR measurement sequence can be executed or not. In particular, as part of the measure of distance, a specific weighting of the different types of machine control and reference control parameters can take place. The use of a measure of distance allows more precise account to be taken of the similarity or dissimilarity between the machine control and reference control parameters.

For example, the determination of the measure of distance can be based on relative deviations of each machine control parameter in relation to the corresponding reference control parameter. For example, the measure of distance can be defined in a simple implementation as the sum of the relative deviations of the machine control parameters in relation to the corresponding reference control parameters. In such a case it can especially still be possible, when there is no identity present between the machine control and reference control parameters, to reliably predict an increased mechanical force flow in the gradient system and if necessary to dispense with carrying out the MR measurement sequence.

It would also be possible, in the determination of the measure of distance for a given relative deviation compared to the corresponding reference control parameter, that an influence of this relative deviation for the echo time TE, the repetition time TR and the number of slices of measured slices on the measure of distance is greater than the influence of these relative deviations for the other control parameters. For example, a 10% deviation of the echo time TE could have the effect that the MR measurement sequence is executed, while a 10% deviation of the pulse duration of the RF pulses has the effect that an MR measurement sequence is not executed, e.g. when all other MR parameters are identical in each case.

This can be based on the knowledge that the echo time TE, the repetition time TR and the number of slices of measured slices have an especially large influence on the increased mechanical force flow in the gradient system, particularly in comparison to the other aforementioned machine control or reference control parameters. Therefore, it can be worth making the effort to dimension the corresponding tolerance range within which the carrying out of the MR measurement sequence is prevented, comparatively small for the echo time TE, the repetition time TR and the number of slices of measured slices, in order to not unnecessarily prevent the carrying out of an MR measurement sequence. By means of such techniques, an especially precise prospective frequency monitoring can take place. In particular, it can be predicted especially well whether, with given machine control parameters, an increased mechanical force flow in the gradient system when carrying out the MR measurement sequence will result.

It can also be possible that a relative deviation of any given machine control parameter in relation to the corresponding reference control parameter, which is greater than a further predetermined threshold value, has the effect that the execution of the MR measurement sequence takes place. In other words, even if the other machine control parameters are identical, the MR measurement sequence can be executed provided in each case one machine control parameter deviates sufficiently from the corresponding reference control parameter. This is based on the knowledge that it is not possible always, or only possible to a restricted extent, to predict the increased mechanical force flow in the gradient system when executing the corresponding MR measurement sequence, provided only one machine control parameter also deviates significantly from the corresponding reference control parameter which indicates the increased mechanical force flow. By such techniques a reliable frequency monitoring can take place that does not excessively sensitively suppress the execution of the MR measurement sequence.

The determination of the measure of distance can further include an weighted averaging of the relative deviations of the machine control parameters in relation to the corresponding reference control parameters. In particular different weights can be used as part of the weighted averaging for the different machine control or reference control parameters. For example, in accordance with the above-mentioned exemplary embodiment, an especially heavy weighting could be given for the echo time TE, the repetition time TR and the number of slices of measured slices, especially by comparison with the weighting of the other machine control or reference control parameters. The weighted averaging allows an especially precise gradation of the influence of the different machine control parameters on the selective execution of the MR measurement sequence. This enables an especially precise prospective frequency monitoring to take place.

Techniques have been predominantly explained above that involve the prospective frequency monitoring, i.e. before the carrying out of the MR measurement sequence. In addition the method can include real-time frequency monitoring. It is possible, for example, for the method to further include, during the execution of the MR measurement sequence, determining a system variable which is indicative for the mechanical flow of force in the gradient system and as a function of the measurement, and storage of the selected machine control parameters in the database. For example the determination of the system variable can take place through a corresponding measurement and/or reading out of system variables during the carrying out of the MR measurement sequence. In a simple embodiment, for example, the applied current strength through the gradient coils can be read out and Fourier transformed in order to obtain the system variable which is indicative for the mechanical force flow in the gradient system. Thus in general the system variable can be a frequency analysis of a current flow through the gradient coils of the gradient system. But it would also be possible, as an alternative or in addition, to measure the gradient fields that are created by the different gradient pulses by a magnetic field sensor and to Fourier transform the measurement variables obtained in this way, in order to once again obtain the system variable.

By techniques such as those described above, it is possible to maintain and to update the sets of reference control parameters contained in the database as long as it can be established, as part of the execution of an MR measurement sequence, that specific machine control parameters lead to the increased force flow through the gradient system. In other words, the prospective frequency monitoring can be combined with a frequency monitoring during the execution of the MR measurement sequence.

In accordance with a further aspect, the invention concerns an MR apparatus that is configured to implement an MR measurement sequence for MR imaging. The MR apparatus includes a processor configured to perform select machine control parameters of the scanner of the MR apparatus, wherein the machine control parameters influence the timing sequence of gradient pulses of the gradient system of the scanner when the MR measurement sequence is executed. The processor is configured to compare the machine control parameters with reference control parameters that are stored in a database accessible by the processor. The reference control parameters indicate an increased mechanical force flow in the gradient system when a corresponding MR measurement sequence is executed. The processor is further configured itself control the operation of the MR scanner so as to selectively execute the MR measurement sequence with the selected machine control parameters as a function of the comparison, or to provide instructions to another control computer for doing so.

For such an MR apparatus effects can be achieved that are comparable to the effects achieved with the inventive method for MR imaging.

The MR apparatus in accordance with the invention aspect can be configured to implement any or all embodiments of the method for MR imaging in accordance with the invention, as described above.

DESCRIPTION OF THE PREFERRED EMBODIMENTS

Figure 1:
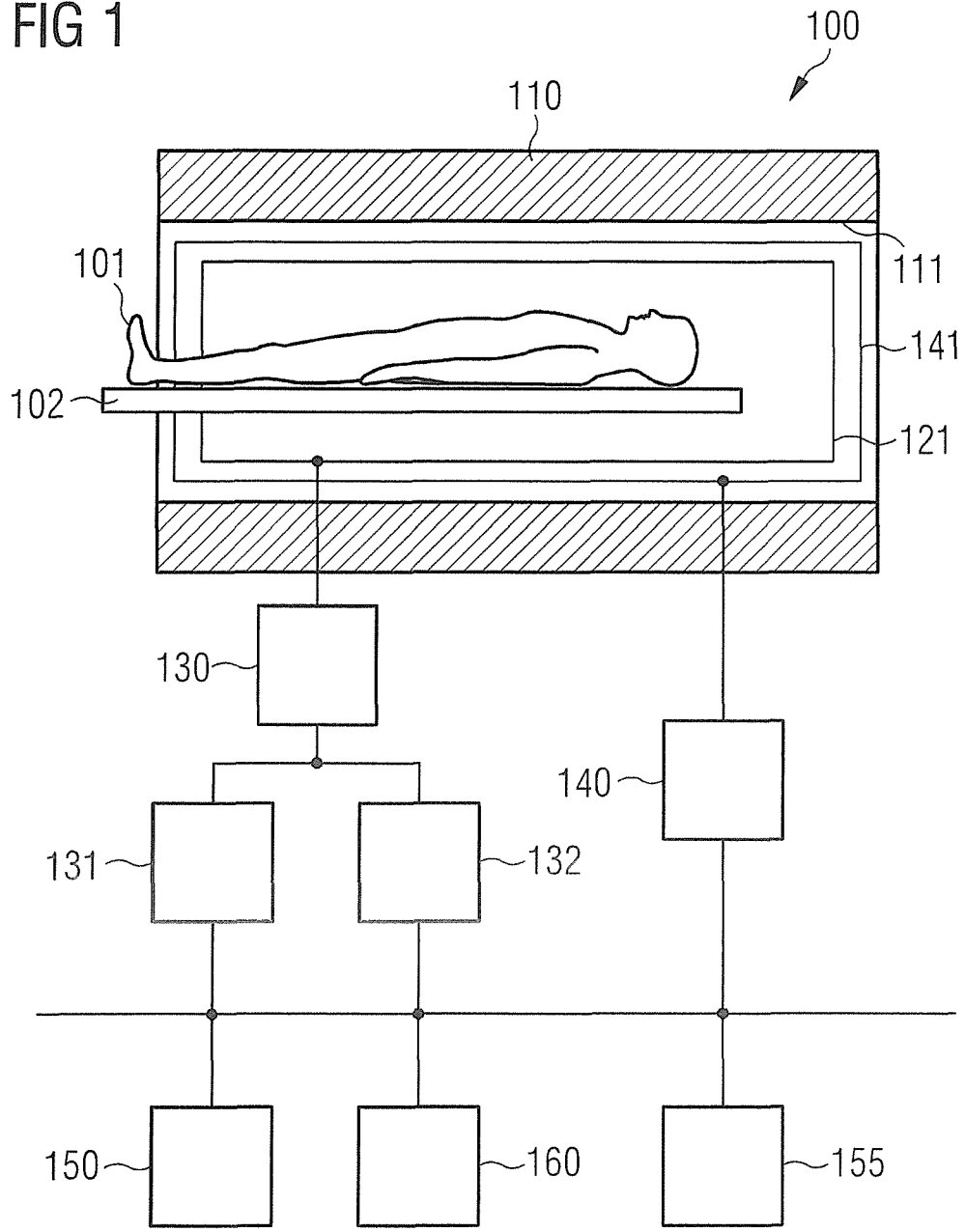
FIG. 1 is a schematic illustration of an MR apparatus that includes a database with stored reference control parameters in accordance with the invention.

The present invention is explained in greater detail below on the basis of preferred forms of embodiment which refer to the drawings. In the figures the same reference characters designate the same or similar elements. The figures are schematic representations of different forms of embodiment of the invention. Elements presented in the figures are not necessarily presented true-to-scale. Instead the various elements shown in the figures are reproduced such that their function and general purpose is understandable to the person skilled in the art. Connections and couplings between functional units shown in the figures can also be implemented as indirect connections or couplings. A connection or coupling can be implemented hard-wired or wirelessly. Functional units can be implemented as hardware, software or as a combination of hardware and software.

Techniques for frequency monitoring of a timing sequence of gradient pulses in MR imaging are explained below. Before an MR measurement sequence is executed there is an automatic search in a database as to whether specific machine control parameters which influence the timing sequence of the gradient pulses when the MR measuring sequence is being carried out are already present in the database in the form of a corresponding set of reference control parameters. Corresponding reference control parameters can be stored in the database if the use of these reference control parameters has led to measurement being aborted during earlier execution of a corresponding MR measurement sequence, for example because of an increased mechanical force flow in the gradient system through excitation of frequencies in a forbidden frequency band. In other words the database can include empirically-determined reference control parameters. The execution of the MR measurement sequence can especially be selectively started when the reference control parameters corresponding to the machine control parameters are not present in the database. Otherwise the execution of the MR measurement sequence is not permitted and the user is accordingly informed thereof. Thus a prospective frequency monitoring can be realized in this way.

Furthermore, if an abortion of a sequence still occurs when the MR measurement sequence is being executed, as a result of an optional real-time frequency monitoring, despite the "approval" of the execution by the comparison of the machine control parameters with the reference control parameters stored in the database, the corresponding set of machine control parameters should be stored as reference control parameters in the database. With future MR measurements it can then be prevented that, as a result of these corresponding machine control parameters, that the execution of that MR measurement sequence is started and then aborted once again.

A situation as described above can be possible because the machine control parameters can cause an increased mechanical force flow largely independently of outside influences such as the patient, the coils used and other disruptive influences. The causality of the excitation of a forbidden frequency band as a function of different control parameters can be especially strong.

FIG. 1 shows an MR scanner 100 configured to implement the inventive techniques, methods and steps, as previously explained. The MR scanner 100 has a magnet 110 that defines a tube 111. The magnet 110 produces a basic magnetic field parallel to its longitudinal axis. The basic magnetic field may exhibit inhomogeneities, i.e. local deviations from a required value. An examination object, here a person 101 being examined, can be pushed on a table 102 into the magnet 110. The MR scanner 100 also has a gradient system 140 for creating gradient fields by switching gradient pulses. The gradient fields are employed for local encoding of MR data acquired as part of the MR imaging. Typically the gradient system 140 has at least three gradient coils 141 able to be activated separately and positioned in a well-defined manner in relation to one another. The gradient coils 141 make it possible to switch the gradient fields in specific spatial directions (gradient axes). The gradient fields can be used for example for slice selection, for frequency encoding (in the read-out direction) and for phase encoding.

For exciting a polarization or alignment of the nuclear spins (or magnetization thereof) produced in the basic magnetic field in the longitudinal direction, a coil arrangement 121 is provided that can irradiate an amplitude-modulated RF excitation pulse into the person 101 being examined. This produces a transverse magnetization of the nuclear spins. To create such RF excitation pulses, an RF transmit unit 131 is connected via an RF switch 130 to the RF coil arrangement 121. The RF transmit unit 131 can include an RF generator and an RF amplitude modulation unit. The RF excitation pulse can flip the transversal magnetization one-dimensionally for a selective slice or two-dimensionally/three dimensionally location-selectively or globally from the rest position.

Furthermore an RF receive unit 132 is coupled by the RF switch 130 to the RF coil arrangement 121. Via the RF receive unit 132 MR signals of the relaxing transversal magnetization can be acquired as MR data, for example by inductive coupling into the RF coil arrangement 121.

The MR scanner 100 is controlled from an operating console computer, 150, which can include a screen, a keyboard, a mouse etc. Via the operating computer 150 a user input can be detected and outputs to the user can be made. For example, via the operating computer 150, individual operating modes or machine control parameters of the MR apparatus can be set by the operator and/or automatically and/or by remote control.

Furthermore the MR scanner 100 is in communication with a processor 155. The processor 155 can be configured, for example, to handle diverse processing operations as part of preparation for executing an MR measurement sequence. In particular the processor 155 can be configured to compare specific machine control parameters, which are applied to the timing sequence of gradient pulses that are to be used as part of the MR measurement sequence, with corresponding reference control parameters stored in a database 160. The reference control parameters that are stored in the database 160 can indicate an increased mechanical force flow in the gradient system 140 when the corresponding MR measurement sequence is being executed. In this way, a prospective frequency monitoring can be carried out in which, even before the execution of the MR measurement sequence, a check is made as to whether an excitation of a forbidden frequency band and thus the increased mechanical force flow in the gradient system 140 is to be expected with specific machine control parameters.

Furthermore the processor 155 can be configured, during the execution of the MR measurement sequence, to define a system variable that is indicative of the mechanical force flow in the gradient system 140. The processor 155 thus can be configured to undertake a real-time frequency monitoring. As a function of the determination of the system variable, the processor 155 can be configured to store the machine control parameters in the database 160. For example, provided the system variable indicates an increased mechanical force flow, thus for example a significant excitation within a forbidden frequency band, the execution of the MR measurement sequence can be aborted and the corresponding machine control parameters can be stored in the database 160.

By such previously described techniques, a frequency monitoring can be performed in which it is possible to prospectively establish the presence of increased mechanical force flow. If a sequence abort has occurred once during the execution of the MR measurement sequence as a result of resonance effects, a repeated sequence abort can be avoided by storing the corresponding machine control parameters as reference control parameters in the database 160.

Figure 2:
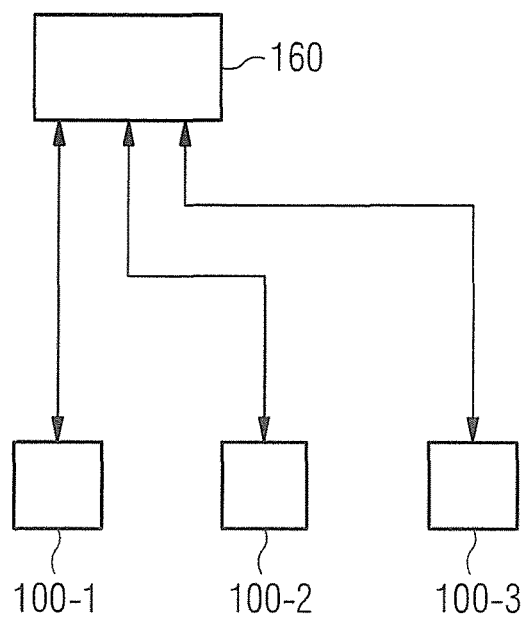
FIG. 2 is a schematic illustration of a number of MR apparatuses coupled to a central database with stored reference control parameters.

Although FIG. 1 shows a scenario in which a local database 160 is provided as part of the MR apparatus 100, it is also possible for the database 160 to be coupled to a number of MR apparatuses 100-1, 100-2, 100-3 (cf. FIG. 2). Then the data collection of reference control parameters that are stored in the database 160 can be comparatively larger and a more exact frequency monitoring is thereby made possible.

Figure 3:
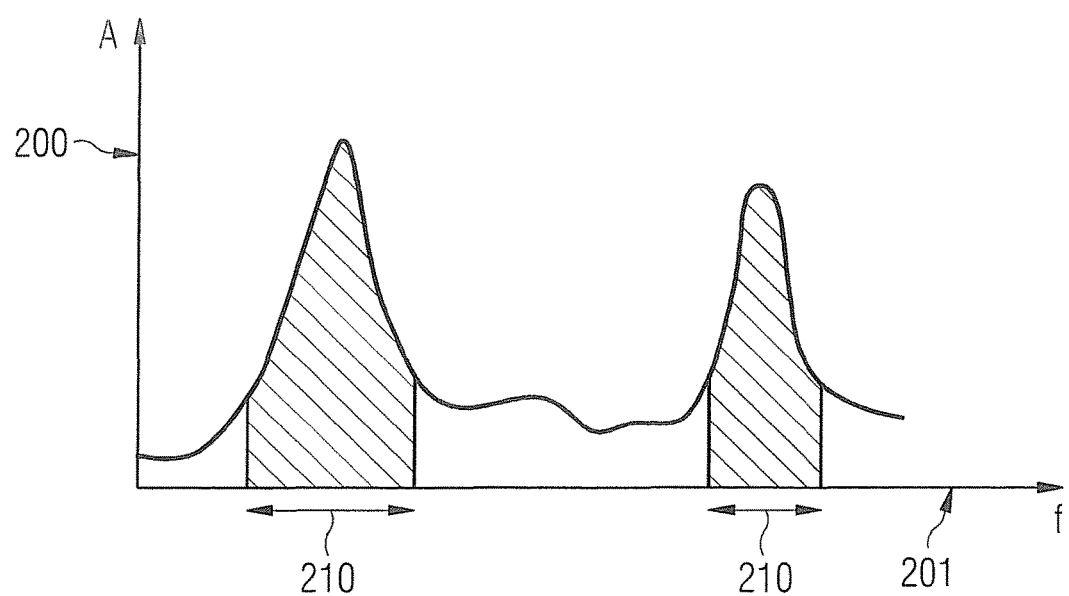
FIG. 3 shows forbidden frequency bands of which the excitation by a timing sequence of gradient pulses results in an increased mechanical flow of force in a gradient system of the MR apparatus.

In FIG. 3 the system variable 200 is plotted against the frequency 201. Furthermore, forbidden frequency bands 210 or resonant areas, in which an increased mechanical force flow in the gradient system 141 results from resonance effects, are graphically highlighted. Provided the system variable 200 indicates an excitation in the forbidden frequency band 210 that exceeds a specific threshold value, the execution of the MR measurement sequence can be aborted, for example, and the corresponding machine control parameters can be stored as reference control parameters in the database 160. For example, the system variable 200 can be a frequency analysis of a current flow through the gradient coils 141 of the gradient system 140; in the case of FIG. 3 this frequency analysis is also weighted frequency-dependently with a response function of the gradient coils 141 in respect of mechanical excitation. As can be seen from FIG. 3, the gradient system 140 reacts in the forbidden frequency bands 210 especially strongly to excitation. Resonances are present here. E.g. the execution of the MR measurement sequence can be aborted, if the system variable 200 exceeds a predetermined threshold value at a given frequency.

Figure 4:
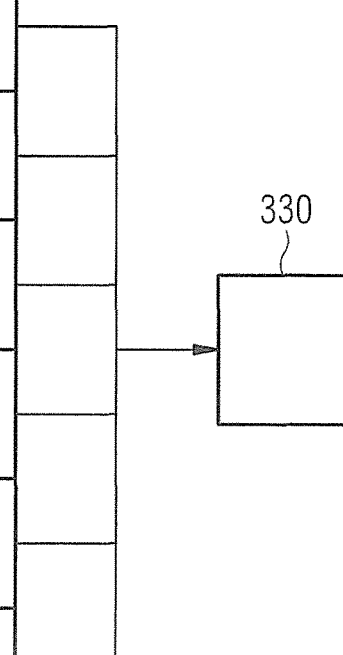
FIG. 4 illustrates the comparison of machine control parameters with reference control parameters stored in a database before the selective carrying out of an MR measurement sequence.

FIG. 4 illustrates the comparison of the machine control parameters 300-1-300-6 with the reference control parameters 310-1-310-6. In FIG. 4 the machine control parameters 300-1-300-6 and reference control parameters 310-1-310-6 plotted in the different rows of the table, read from top to bottom, each represent the echo time TE, the repetition time TR, the number of slices of measured slices, the slice thickness of measured slices, the bandwidth and the pulse duration of RF pulses. For example a number of sets of the reference control parameters 310-1-310-6, i.e. each with different values, can be stored in the database.

In the scenario of FIG. 4 the comparison includes the determination of a measure of distance between machine control parameters 300-1-300-6 and the reference control parameters 310-1-310-6. In particular the relative deviations 320-1-320-6 of each machine control parameter 300-1-300-6 compared to the corresponding reference control parameters 310-1-310-6 are determined. As can be seen from FIG. 4, individual machine control parameters 300-1-300-6 exhibit a deviation compared to the corresponding reference control parameters 310-1-310-6. In a simple identity comparison between the machine control parameters 300-1-300-6 and the corresponding reference control parameters 310-1-310-6, lack of identity would therefore be established and the carrying out of the MR measurement sequence with the corresponding machine control parameters 300-1-300-6 could take place. The measure of distance 330 can, for example, be computed however as part of a weighted averaging of the relative deviations 320-1-320-6 and thus also take account of the deviations 320-1-320-6 in a quantified manner. Here it would be possible, for example, to take particularly strong account of the deviations 320-1-320-4, i.e. especially more strongly than the deviations 320-5 and 320-6. This can be the case since the echo time 300-1, 310-1, the repetition time 300-2, 310-2, the number of slices of measured slices 300-3, 310-3, and also the slice thickness of measured slices 300-4, 310-4 have an especially strong influence on the increased mechanical force flow in the gradient system 141. It would also be possible for a relative deviation 320-1-320-6 of a given machine control parameter 300-1-300-6 in relation to the corresponding reference control parameters 310-1-310-6 which is greater than a predetermined threshold value, to have the effect that the carrying out of the MR measurement sequence takes place. In the example of FIG. 4 for example the 14% deviation of the machine control parameter 300-3 from the corresponding reference control parameter 310-3 could have the effect that the MR measurement sequence is executed in any event.

Figure 5:
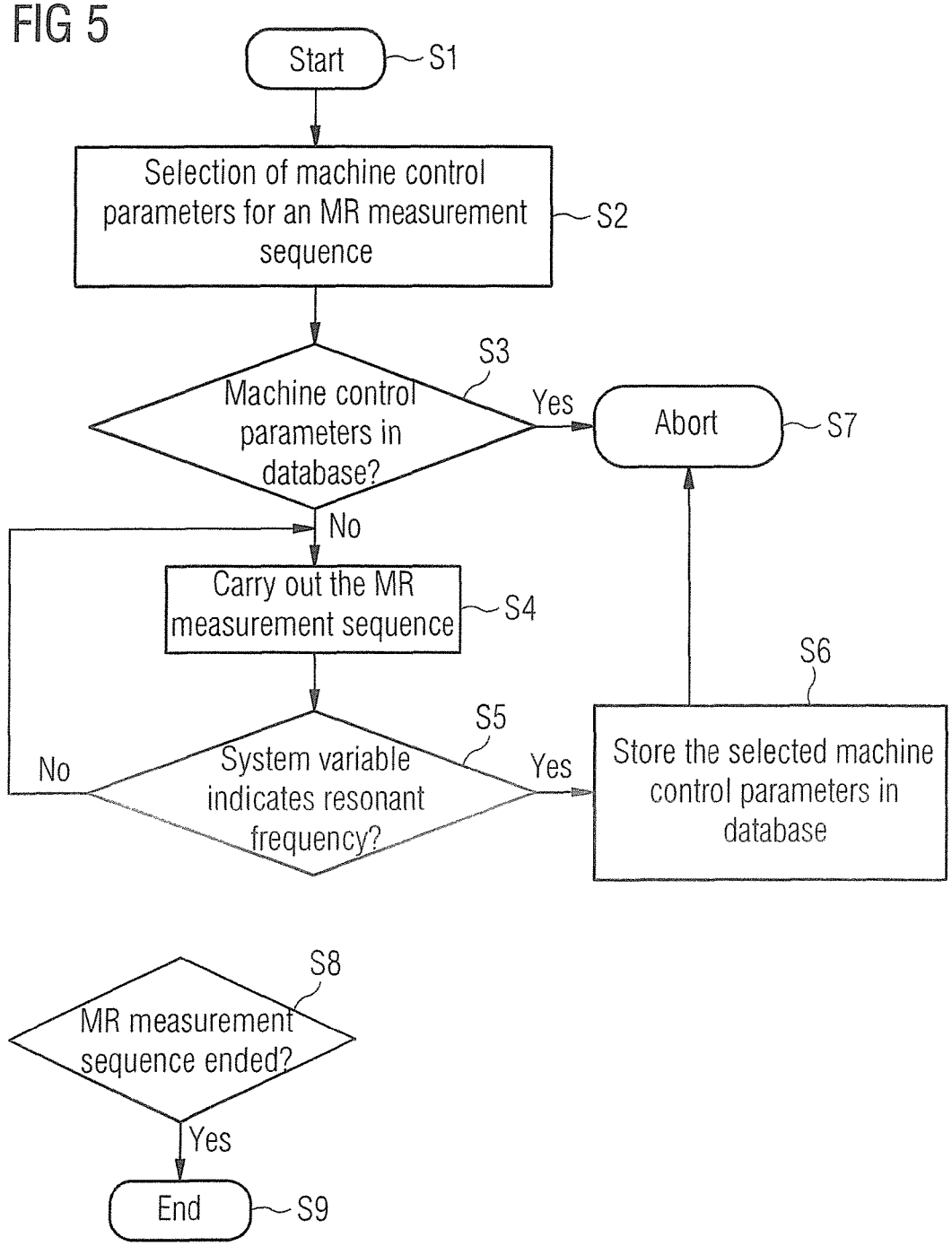
FIG. 5 is a flowchart of the basic steps of the inventive method for MR imaging.

FIG. 5 shows a flowchart of a method for MR imaging in accordance with different forms of embodiment. The method begins in step S1. Initially, in step S2, a set of machine control parameters 300-1-300-6 for the MR measurement sequence is selected. Then a check is made in step S3 as to whether these machine control parameters 300-1-300-6 are present in the database 160. For example, as part of step S3, a simple identity comparison can take place or the measure of distance 330 can be calculated. If the machine control parameters 300-1-300-6 are to be found in the database 160, then the measurement is aborted in step S7. This means that the MR measurement sequence is not executed. If, however, it is established in step S3 that the machine control parameters 300-1-300-6 are not found in the database, i.e. that no comparable set of reference control parameters 310-1-310-6 is present in the database 160, then the method is continued with step S4. In step S4 the MR measurement sequence is executed. During the carrying out of the MR measurement sequence in step S4, in a step S5 in each case the system variable 200 is determined which is indicative for the mechanical force flow in the gradient system 141. A check is made as to whether the system variable indicates an increased mechanical force flow, i.e. whether a significant excitation within a forbidden frequency range 210 is present. If this is not the case, the MR measurement sequence continues to be executed (cf. step S4). Otherwise the machine control parameters 300-1-300-6 are stored in the database 160 as a further set of reference control parameters 310-1-310-6 (step S6) and the execution of the MR measurement sequence is aborted (step S7). If the MR measurement sequence is not ended by an unplanned abortion in step S7, it is ended by complete processing of the corresponding measurement protocol (steps S8, S9).

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for operating a magnetic resonance (MR) imaging apparatus, comprising an MR scanner configured to receive an examination subject therein, and a control computer configured to operate the MR scanner to acquire MR data from the examination subject therein, said MR scanner comprising a gradient coil system, said method comprising:

entering control parameters into said control computer that influence a timing sequence of gradient pulses emitted by said gradient coil system during the acquisition of said MR data;

from said control computer, retrieving reference control parameters from a database that designate a degree of mechanical force flow that occurs in said gradient coil system when said MR scanner is operated to acquire MR data using the reference control parameters;

in said control computer, comparing the control parameters to the reference control parameters with respect to a comparison criterion that designates an acceptable level of said mechanical force flow in said gradient coil system during the acquisition of said MR data;

in said control computer, automatically determining, dependent on said comparing, whether said magnetic resonance data should be acquired by operating said MR scanner according to the control parameters that were entered into said control computer; and from said control computer, only if said determining produces a determination result that said MR data should be acquired by operating said MR scanner according to the control parameters that were entered into said control computer, then formulating or selecting an MR data acquisition sequence from said control parameters and proceeding to operate said MR scanner to acquire said MR data according to said MR data acquisition sequence.

2. A method as claimed in claim 1 comprising selecting said control parameters from the group consisting of an echo time of MR signals produced by said MR data acquisition sequence, a repetition time of said MR data acquisition sequence, a number of slices of the examination subject from which said MR data are to be acquired, a slice thickness of respective slices of the examination subject from which said MR data are to be acquired, a bandwidth for readout of said MR data, a type of MR data acquisition sequence that is to be used for acquiring said MR data, a pulse duration of radio-frequency pulses in an MR data acquisition sequence to be used for acquiring said MR data, a resolution of said MR data, an amplitude of said gradient pulses, a current strength of current in gradient coils of said gradient coil system in order to produce said gradient pulses, a switching rate of gradient coils in said gradient coil system in order to produce said gradient pulses, and a type of said MR scanner.

3. A method as claimed in claim 1 wherein comparing said control parameters with said reference control parameters comprises determining a magnitude of a difference between said control parameters and said reference control parameters and comparing said difference to a threshold value, and wherein said determining comprises determining said whether said MR data should be acquired by operating said MR scanner according to said control parameters that were entered into said computer dependent on a relationship of said difference to said threshold value.

4. A method as claimed in claim 3 wherein each of said control parameters has a corresponding reference control parameter among said reference control parameters, and wherein determining said difference comprises determining a deviation between each control parameter and the corresponding reference control parameter.

5. A method as claimed in claim 4 wherein said control parameters comprise a control parameter that sets an echo time for acquiring said MR data, a control parameter that sets a repetition of an MR acquisition sequence for acquiring said MR data, and a control parameter that sets a number of slices from which said MR data are to be acquired, said method comprising, for a selected control parameter among said control parameters, using, as said threshold value, a value that designates whether an influence of the deviation of the selected control parameter from its corresponding reference control parameter on said echo time for acquiring said MR data, or said repetition of an MR data acquisition sequence for acquiring said MR data, or said number of slices from which said MR data are to be acquired, is greater than said influence for other control parameters in said plurality of control parameters.

6. A method as claimed in claim 5 comprising, in said control computer, determining that said MR data should be acquired from the examination subject by operating the MR scanner according to the control parameters entered into said control computer when said threshold value is exceeded.

7. A method as claimed in claim 4 comprising, in said control computer, implementing a weighted averaging of the respective deviations in order to determine said difference.

8. A method as claimed in claim 1 comprising:
in said control computer, determining a system variable of said MR scanner that is indicative of said mechanical force flow occurring in said gradient coil system during the acquisition of said MR data by operating said MR scanner according to said MR data acquisition sequence; and
dependent on said system variable, storing the control parameters in said database that were entered into said control computer and that resulted in said MR data acquisition sequence.

9. A magnetic resonance (MR) apparatus comprising:
an MR scanner configured to receive an examination subject therein, said MR scanner comprising a gradient coil system;
a control computer configured to operate said MR scanner to acquire MR data from the examination subject therein;
said control computer being configured to receive control parameters, as an input, that influence a timing sequence of gradient pulses emitted by said gradient coil system during the acquisition of said MR data;
said control computer being configured to retrieve reference control parameters from a database that designate a degree of mechanical force flow that occurs in said gradient coil system when said MR scanner is operated to acquire MR data using the reference control parameters;
said control computer being configured to compare the control parameters to the reference control parameters with respect to a comparison criterion that designates an acceptable level of said mechanical force flow in said gradient coil system during the acquisition of said MR data;
said control computer being configured to automatically determine, dependent on the comparison, whether said magnetic resonance data should be acquired by operating said MR scanner according to the control parameters that were entered into said control computer; and
said control computer, only if the determination produces a determination result that said MR data should be acquired by operating said MR scanner according to the control parameters that were entered into said control computer, being configured to then formulate or select an MR data acquisition sequence from said control parameters and to proceed to operate said MR scanner to acquire said MR data according to said MR data acquisition sequence.

* * * * *